United States Patent [19]

Chase et al.

[11] 4,254,511
[45] Mar. 10, 1981

[54] INTRAOCULAR LENS WITH NONCIRCULAR EYE ENGAGING RETENTION MEANS

[75] Inventors: Charles P. Chase, Brea; William J. Link, Irvine, both of Calif.

[73] Assignee: Heyer-Schulte Corporation, Goleta, Calif.

[21] Appl. No.: 60,530

[22] Filed: Jul. 25, 1979

[51] Int. Cl.³ .......................... A61F 1/16; A61F 1/24
[52] U.S. Cl. ........................................................ 3/13
[58] Field of Search ........................................ 3/13, 1

[56] References Cited

U.S. PATENT DOCUMENTS

| | | | |
|---|---|---|---|
| 3,925,825 | 12/1975 | Richards et al. | 3/13 |
| 4,012,823 | 3/1977 | Richards | 3/13 X |
| 4,077,071 | 3/1978 | Freeman | 3/13 |
| 4,092,743 | 6/1978 | Kelman | 3/13 |
| 4,104,339 | 8/1978 | Fetz et al. | 3/13 X |
| 4,168,547 | 9/1979 | Konstantinov et al. | 3/13 |
| 4,173,798 | 11/1979 | Welsh | 3/13 |
| 4,174,543 | 11/1979 | Kelman | 3/13 |

FOREIGN PATENT DOCUMENTS 2725219 12/1978 Fed. Rep. of Germany ............... 3/13

OTHER PUBLICATIONS

"The Weightless Intraocular Lens" by Richard C. Troutman, Ophthalmic Surgery, vol. 8, No. 3, Jun. 1977, pp. 153–155.
"A Weightless Iseikonic Intraocular Lens" by Richard D. Binkhorst et al., American Journal of Ophthalmology, vol. 58, No. 1, Jul. 1964, pp. 73–78.

*Primary Examiner*—Ronald L. Frinks
*Attorney, Agent, or Firm*—Larry N. Barger

[57] ABSTRACT

An intraocular lens with an iris retention loop that is attached to an optical section of the lens by a pair of shank sections. Each shank section has a noncircular cross sectional area to provide a more flattened contact surface for engaging an inner edge of the iris. Such structure reduces cutting of the iris when the iris is stretched over these shank sections to retain the lens in the eye.

8 Claims, 5 Drawing Figures

INTRAOCULAR LENS WITH NONCIRCULAR EYE ENGAGING RETENTION MEANS

BACKGROUND

Intraocular lenses are frequently surgically implanted in the eye to replace the natural lens that has been removed. The removal of the natural lens is a typical surgical procedure to repair a cataract.

A typical intraocular lens has a magnifying optical section usually made of polymethylmethacrylate (PMMA) to which is attached retention loops or other structure for securing the optical section to the eye. One common procedure is to implant the optical section in the anterior section immediately in front of the iris. A plurality of retention loops are secured to a rear of the optical section by upstanding shank sections. The iris loops are placed behind the iris, and the shank sections engage an inner edge of the iris to prevent lateral shifting of the lens in the eye so that it can properly focus. The Fedorov et al U.S. Pat. No. 3,673,616 shows schematically how an intraocular lens is attached to the iris.

Because the iris retention loops and shanks are of an extremely small diameter, i.e. 0.005 to 0.010 inch, their circular cross section in the shank area tends to cut into the inner edge of the iris in the same manner as a wire cheese cutter. This is a particular problem when the iris is stretched over the shank sections.

SUMMARY OF THE INVENTION

This invention overcomes the above problems by providing a surface of the shank section that contacts the iris with a curvature that is substantially more flattened to give more area of contact with the iris to reduce cutting. In a preferred embodiment, the shank sections are of a noncircular cross section, such as oval, with the more flattened side of the oval facing outwardly for contacting an inner edge of the iris. In an alternate embodiment, the loop and shank sections are not formed of a constant diameter monofilament. Instead they are molded with an enlarged diameter shank section and a loop section of conventional diameter.

THE DRAWINGS

DETAILED DESCRIPTION

Figure 1:
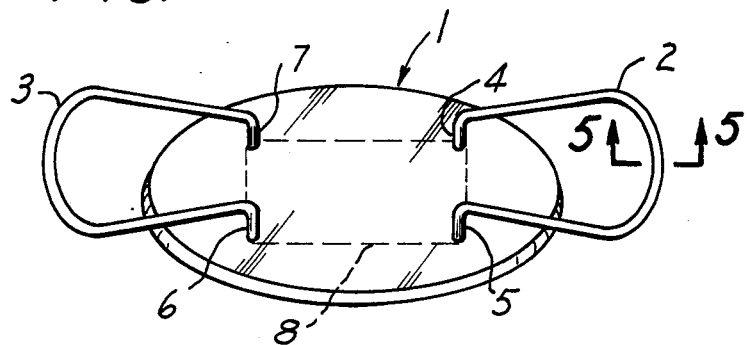
FIG. 1 is a rear prospective of an intraocular lens.

FIG. 1 shows a rear prospective of a typical intraocular lens which has an optical section having opposed faces extending between a peripheral edge designated generally as 1. To this optical section are secured a plurality of iris retention loops 2 and 3 that have shank sections 4, 5, 6, and 7 spaced inwardly from the peripheral edge. The dotted line 8 is a schematic showing of where an inner edge of the iris is positioned around a central viewing area of the optical section 1 when the iris is maintained between the loops 2 and 3 and the optical section. Preferably, the shank sections are approximately equally spaced around a central viewing area.

It is understood that the shape, number, and configuration of the iris retention loops are merely illustrative. Many other different loop configurations, etc. could be used within the scope of this invention.

Figure 2:
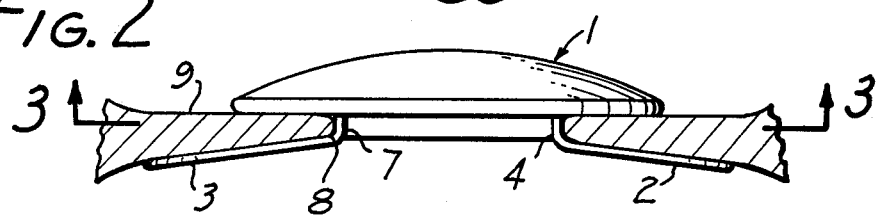
FIG. 2 is a side elevational view of the lens of FIG. 1 showing it attached to an iris.

FIG. 2 shows an iris 9 retained between the optical section 1 and loops 2 and 3. It is seen that the shank sections, such as 4 and 7, engage an inner edge 8 of the iris. It is at this inner edge that previous intraocular lenses had a problem of cutting the iris.

Figure 3:
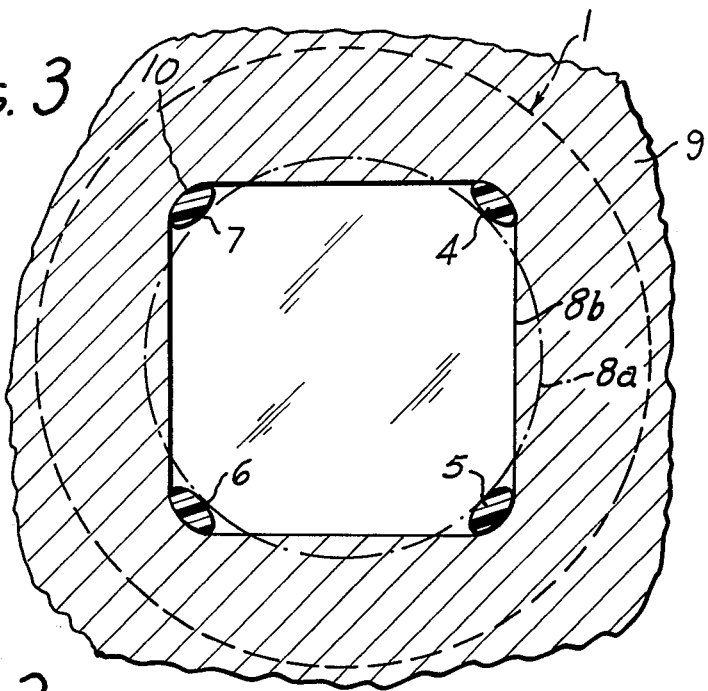
FIG. 3 is a sectional view taken along line 3—3 of FIG. 2 showing a first embodiment of the improved lens.

The sectional view of FIG. 3 shows iris 9 with an inner edge 8a showing at the dotted line the natural generally circular configuration of the inner edge of the iris. Solid line 8b shows a somewhat more stretched and rectangular shape of the inner edge of the iris once the lens has been surgically implanted. It is understood that there can be a wide variance in the degree of stretching at the inner edge of the iris with different implantations. On some patients, the inner edge of the iris will be stretched very little.

In the first embodiment of the invention shown in FIG. 3, the shank sections 4, 5, 6, and 7 have outer surfaces, such as at 10, that are more flattened or have a larger radius of curvature than a circular shank section with the cross sectional area. As shown in FIG. 3, the shank sections are oval. Preferably, the longitudinal dimension is at least 1.5 times the narrower dimension of the oval shank section. It is understood that other non-circular configurations could be used instead of the oval configuration to provide the additional area of contact with the iris to reduce the "cheese cutter" effect.

Figure 4:
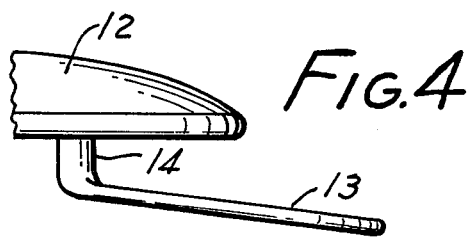
FIG. 4 is an enlarged fragmentary side view showing a second embodiment of the iris loop and shank sections.

In FIG. 4, a second embodiment of the invention is shown in which an optical section 12 has a retention loop 13 secured to the optical section by a shank section 14. It is seen that shank section 14 has a substantially larger diameter, preferably more than 1.5 times larger, than the loop 13. Thus, if desired, both the loop and its shank section can be of circular cross section without substantially increasing the weight and bulkiness of the loop section. In the second embodiment, it is understood that the loop and shank sections would be formed by other processes than constant diameter filament extrusion to produce the different diameter sections.

In both of the embodiments in the attached drawings, the size and weight of the retention loops and shanks have not been substantially changed from previous lenses. This is important for controlling the specific gravity of the combined optical section, the loop, and its shank sections. The optical section is normally made of polymethylmethacrylate (PMMA) which has specific gravity of 1.19 relative to the aqueous humor which has a specific gravity of approximately 1.0. The loop and its shank sections, commonly made of polypropylene, have a specific gravity of 0.91. Thus, the polypropylene material tends to float in the aqueous humor, while the PMMA material tends to sink. By controlling the ratio of the amounts of polypropylene and PMMA in the complete intraocular lens, the combined specific gravity of the lens can be controlled.

It has been found desirable to have the intraocular lens with a combined specific gravity slightly greater than the aqueous humor so that gravity can be employed for positioning the lens both during and after surgery. In some medical procedures, the ophthalmologist operates on the patient's eye while the cornea is facing downwardly to take advantage of gravity in positioning the lens. Very large buogant loops are undesirable. On the other hand, the complete lens should not have a specific gravity much greater than the aqueous humor because a sudden jerking of the patient's head after implantation could cause a dislocation of the lens due to inertia.

Also, it is advantageous to keep the iris retention loops, as well as their shank sections, as small as possible to minimize interference with the biological functioning of the eye. Because of this and the reasons explained above, it is not convenient simply to increase the diameter of a constant diameter extruded monofilament material used to form the loop and shank sections.

Figure 5:
FIG. 5 is a sectional view taken along line 5—5 of FIG. 1.

In describing the first and second embodiments of the invention, primary emphasis has been laid to the shank section's contact with the inner edge of the iris. This is because the inner edge is where most of the problems of the "cheese cutter" effect occur. It is also considered part of this invention to provide a noncircular, such as oval, cross sectional profile of the loop section itself. FIG. 5 shows such loop section 2 with a more flattened surface 15 adapted to contact the inner (posterior) face of the iris.

In the foregoing description, specific examples have been used to describe the invention. However, it is understood by those skilled in the art that certain modifications can be made to these examples without departing from the spirit and scope of the invention.

We claim:

1. An intraocular lens comprising: an optical section of a first material, which optical section has opposed faces extending between a peripheral edge; a rod-like retaining member of a different second material, which rod-like retaining member is free of attachment with the optical section's peripheral edge and has an integral shank with at least one end attached at a specific location to the optical section spaced inwardly from said peripheral edge; and this shank has a noncircular cross section with a flattened area oriented in a particular direction so as to engage an inner edge of an iris when the intraocular lens is surgically implanted in an eye.

2. An intraocular lens as set forth in claim 1, wherein the optical section is of a material that has a specific gravity greater than aqueous humor, and the retention member is of a material having a specific gravity less than aqueous humor for controlling the overall buoyancy of the intraocular lens.

3. An intraocular lens as set forth in claim 2, wherein the optical section is of polymethylmethacrylate and the rod-like retention member is of polypropylene.

4. An intraocular lens as set forth in claim 1, wherein a pair of spaced apart shanks are integrally connected in a one-piece construction to a loop.

5. An intraocular lens as set forth in claim 4, wherein the shanks are attached to one face of the optical section at a distance spaced inwardly from the optical section's peripheral edge, and these shanks extend from such face in a direction approximately perpendicular to such face.

6. An intraocular lens as set forth in claim 1, wherein the shank has a generally oval cross section with the more flattened convex surface of such shank adapted to engage an inner edge of an iris.

7. An intraocular lens as set forth in claim 6, wherein there are four shanks with generally oval cross sections to distort an iris aperture from a generally circular shape to a generally rectangular shape without substantial cutting into an inner edge of such iris at the corners of the rectangularly distorted iris.

8. An introacular lens comprising: an optical section of a material having a specific gravity greater than aqueous humor and having a pair of opposed faces extending between a peripheral edge; a rod-like retaining member of a different material having a specific gravity less than the aqueous humor for controlling the overall buoyancy of the intraocular lens, with the rod-like retaining member being free of attachment with the optical section's peripheral edge and having a pair of iris inner edge engageable shanks integrally connected to a loop, said shanks being attached at specific locations to the optical section spaced inwardly from said peripheral edge; and each shank has a generally circular cross-sectional area that is substantially greater than the cross-sectional area of the loop, whereby relatively large sized shanks can be used to reduce cutting of an inner edge of an iris without causing the retention member to undesirably increase the overall buoyancy of the intraocular lens.

* * * * *